United States Patent [19]

Homsy

[11] 4,118,532
[45] Oct. 3, 1978

[54] IMPLANTABLE MATERIAL AND METHOD OF PREPARING SAME

[76] Inventor: Charles A. Homsy, 11526 Raintree Cir., Houston, Tex. 77024

[21] Appl. No.: 758,499

[22] Filed: Jan. 11, 1977

Related U.S. Application Data

[63] Continuation-in-part of Ser. No. 300,246, Oct. 24, 1972, abandoned.

[51] Int. Cl.² ............................................. A61F 1/24
[52] U.S. Cl. ................................. 428/294; 3/1; 128/68; 128/78; 128/82; 260/42.17; 260/42.27; 260/900; 260/897 C; 428/288; 428/297; 428/367; 428/368; 428/323; 428/327; 428/408; 428/422; 428/902
[58] Field of Search ............... 161/162, 189, 170, 176; 128/68, 78, 82; 260/42.27, 42.17, 900, 897 C; 428/294, 297, 288, 422, 367, 902, 323, 327, 368, 408

[56] References Cited

U.S. PATENT DOCUMENTS

| 2,400,099 | 5/1946 | Brubaker | 428/422 |
|---|---|---|---|
| 2,578,523 | 12/1951 | Llewellyn | 428/422 |
| 3,056,709 | 10/1962 | Rising | 428/422 |
| 3,124,502 | 3/1964 | Radke | 428/422 |
| 3,320,107 | 5/1967 | Christenson | 428/422 |
| 3,486,961 | 12/1969 | Adams | 428/422 |
| 3,674,432 | 7/1972 | Margrave | 23/205 |
| 3,992,725 | 11/1976 | Homsy | 428/422 |

FOREIGN PATENT DOCUMENTS

| 655,193 | 1/1963 | Canada. | |
| 837,198 | 3/1966 | United Kingdom. | |
| 1,228,573 | 4/1971 | United Kingdom | 428/422 |

OTHER PUBLICATIONS

"Method Harnesses Direct Fluorination," *C & EN*, vol. 48, No. 2, Jan. 12, 1970, pp. 40 & 41.

*Primary Examiner*—Ellis Robinson
*Attorney, Agent, or Firm*—Vinson & Elkins

[57] ABSTRACT

A composition of material suitable for in vivo implantation to provide a wear surface which composition includes carbon fibers, perfluorocarbon fibers, fluorinated carbon fibers, fluorinated carbon particles, fluorinated hydrocarbon fibers, fluorinated hydrocarbon particles, polytetrafluoroethylene fibers or combinations thereof and polytetrafluoroethylene resins alone or with a high molecular weight polyethylene all of which composition is processed to align a substantial portion of the fibers with the wear surface. The preferred method of preparing such composition of material includes the steps of mixing, filtering, compressing, rolling, sintering and drying.

13 Claims, No Drawings

IMPLANTABLE MATERIAL AND METHOD OF PREPARING SAME

CROSS REFERENCE TO RELATED APPLICATIONS

The present application is a continuation-in-part of my prior copending appliction Ser. No. 300,246, filed Oct. 24, 1972 now abandoned.

SUMMARY

The present invention relates to an improved composition of matter suitable for in vivo implantation as a wear surface and to the method of preparing such composition of material.

An object of the present invention is to provide an improved composition of material suitable for in vivo implantation which exhibits high resistance to wear.

Another object is to provide an improved wear material which has low friction and is highly resistant to wear.

A further object is to provide an improved wear material which when subjected to frictional movement has minimum galling and releasing of particles responsive thereto.

Still another object is to provide an improved method of preparing a wear material of fibers and resin so that the fibers are generally aligned with the wear surface.

A still further object is to provide an improved composition of material for in vivo implantation which may be sterilized by the usual sterilization procedures and apparatus, such as a steam autoclave, without being adversely affected thereby.

Still another object is to provide an improved composition of material for in vivo implantation which in addition to the above desired features of having low friction and substantial resistance to wear is white in color.

These and other objects and advantages of the present invention are hereinafter set forth and explained.

DESCRIPTION OF THE PREFERRED EMBODIMENTS

A wear material suitable for in vivo implantation is adapted to be sterilized in a steam autoclave, does not include anything which would be toxic or cause a body reaction and has a surface exhibiting low friction and high resistance to wear.

One preferred form of wear material of the present invention includes carbon fibers and a resin such as polytetrafluoroethylene which are prepared in a manner to position the carbon fibers in generally parallel relationship to the surface of the wear material.

This wear material which has been found suitable for implantation as hereinbefore described has a composition of more than 15 percent by volume to 65 percent by volume carbon fibers and particles and less than 85 percent by volume to 35 percent by volume of polytetrafluoroethylene resins such as is marketed by Du Pont as their TFE resin.

A preferred composition of material for implantation is 40 percent by volume fibrous carbon or graphite and 60 percent by volume of the TFE fluorocarbon polymer. A composition which has exhibited excellent wear properties and low friction is one containing 30 percent by volume fibrous carbon or graphite, 10 percent by volume particulate carbon or graphite and 60 percent by volume TFE polymer. Generally it is preferred that the ratio of total fibrous and particulate carbon to fibrous carbon be from 1 to 1 to 5 to 1.

A specific preferred composition providing 40% by volume carbon fiber filler includes graphite fiber sold by Carborundum Company under the name GY 2F, 12.0 grams; Du Pont Teflon, TFE-6 Resin, 2.76 grams; and Du Pont Teflon, TFE-7 Resin, 24.8 grams. Another useful composition providing 40% by volume fluorinated carbon fiber includes fluorinated graphite fiber prepared by Marchem Company, Houston, Texas, 19.6 grams, Du Pont Teflon TFE-6 Resin, 2.76 grams, and Du Pont Teflon, TFE-7 Resin, 24.8 grams. Another useful composition includes graphite fiber sold by Carborundum Company under the name GY 2F, 10.8 grams, particulate carbon sold by Biocarbon, Tarzana, California (technically described as vitreous carbon frit), 3.6 grams, Du Pont Teflon, TFE-6 Resin, 2.8 grams, Du Pont Teflon, TFE-7 Resin, 25 grams. This Composition provides 30% by volume carbon fiber filler and 10% by volume particulate carbon filler.

The wear composition is prepared by mixing the resin and carbon or graphite with a suitable solvent such as isoparaffinic hydrocarbon in a high speed, high shear mixer. The amount of solvent is adjusted to the size of the mixer. For example, in a mixer of 500 milliliters, 375 milliliters of solvent is used for dry ingredients weighing approximately 50 grams. Mixing is carried out until a complete uniform slurry is produced.

The mixed slurry is filtered. The filtration is preferred to be by vacuum filter such a Buechner funnel, and should proceed until the residual solvent left in the filter cake is less than approximately 20 percent by weight.

Following filtration, the filter cake is placed between the platens of a heated press and is compressed at levels of from 500 to 3,000 psi and at a temperature between 100° F. and 250° F. for periods from 1 to 5 minutes. The conditions are adjusted so that the solvent level after compression is less than 15 percent by weight. Optionally, the compressed filter cake may be dried in an oven to remove all solvent at temperatures between 150° F. and 500° F. and for times up to several hours.

Next, the compressed filter cake is run through the nip of heated rolls which are heated to a temperature between 100° F. to 250° F. This temperature is adjusted to the particular volatility of the solvent. The thickness of the cake is reduced in decrements of approximately 20/1000ths of an inch to a thickness between 20/1000ths and 60/1000ths of an inch.

When the desired thickness is reached, the temperature of the rolls is elevated to between 280° F. and 360° F. and the thickness of the material during each subsequent pass is reduced to one-half of its thickness. To maintain the desired thickness, the sheet of material is doubled after each pass and then is run through the next pass at 90° to the previous pass. This procedure may be carried out from four to eight times depending on the apparent toughness of the product at a given stage of rolling. It may be desirable to roll down to one-half original thickness in steps of 5/1000ths or 10/1000ths of an inch.

It should be noted that the sheet material produced by the preceding rolling step can be formed into particular shapes if desired by compression molding, vacuum drawing, and other shaping operations at relatively low pressures and the shaped material can then be compression sintered in an appropriate mold to retain such shape.

When the rolling is completed, the material is sintered at a temperature from 610° F. to 680° F. for periods from 30 minutes to several hours depending on the thickness of the stock. It should be noted that if the product contains residual solvent which is slow to evaporate, extended periods of drying at temperatures from 300° F. to 500° F. may be used prior to sintering to assure removal of the solvent. When fluorinated particulated filler are used, it is recommended that the solvent be removed before rolling since difficulty may be encountered with blistering of the sheet stock during sintering if the solvent is not removed. In certain materials which are difficult to dry it may be desirable to vacuum dry the filter cake before rolling to avoid the blistering problem.

If desired, the sintering step may be a pressure sintering step in which the material is placed between the platens of a heated press at a temperature in the range from 640° F. to 740° F., preferably 700° F. at a pressure in the range from 50 p.s.i. to 5,000 p.s.i., preferably 2,000 p.s.i. and for a period of time from 1 to 30 minutes, preferably 5 minutes. The material is moved directly from the press and rapidly cooled by forced air connection or immersion in a room temperature water bath. This pressure sintering may be used in place of or in addition to the above described sintering step. This technique may also be used to prepare multi-ply laminates from unsintered stock.

The preferred forms of such wear material include the fibrous carbon. This material has improved wear properties and low friction. It is believed that the reason for such improved properties results from the orientation of the carbon fibers to a position generally parallel to the wear surface. In such position, the carbon fibers would not have a tendency to break off and thereby create an extreme wear problem and further since the carbon fibers have a low coefficient of friction, the exposure of the carbon fibers on the wear surface would not cause a drastic increase in friction as might be expected with other materials.

The improved wear material may use for its matrix any perfluorinated high polymer such as polytetrafluoroethylene (Teflon TFE), a polyhexafluoropropylene or a co-polymer of hexafluoropropylene and tetrafluoroethylene which is commercially available from Du Pont under the name Teflon FEP resin or mixtures of such polymers.

Also if desired, the reinforcing additive may be carbon fibers, perfluorocarbon fibers, fluorinated carbon fibers, fluorinated carbon particles or a combination of two or more of the foregoing types of carbon fibers. The use of the fluorinated carbon fibers is advantageous since the fluorination reduces the critical surface tension of the fibers to the order of 20 dynes per centimeter thereby more closely matching the critical surface tension of the matrix polymer. This matching provides substantially greater adhesion between the matrix polymer and the reinforcing additive. The fluorinated carbon fibers are also believed to be advantageous as the fluorination changes the surface of the carbon fibers to further reduce the friction in the wear material.

In such matching of surface tension of the reinforcing additive or filler and the matrix polymer. They may both be selected to have the same critical surface tension or either may be processed to match the other. For example, polytetrafluorocarbon fibers and particles may be used with a perfluorocarbon matrix. Examples of such processing of the latter type of material would be fibers and particles of carbon, hydrocarbon or other organic material (such as polyimide) which have been treated to have a surface fluorination. The process of fluorinating the surface of carbon materials is known and is disclosed in the J. L. Margrave et al. U.S. Pat. No. 3,674,432, issued July 4, 1972 and in the article "Method Harnesses Direct Fluorination" appearing in the Jan. 12, 1970 edition of Chemical & Engineering.

It has been found that a suitable material may be provided by a composition of a filler element such as a fluorinated carbon or a fluorinated hydrocarbon or a fluorinated organic material (such as fluorinated polyimide) in either particulate or fibrous form and a sintered perfluorinated high polymer resin retaining said filler element in the structure.

Another preferred composition of wear material may be produced utilizing a high molecular weight polyethylene (HMWPE) in certain formulations. For example, very suitable materials were produced from the following recipes:

(a) 20% (Vol.) carbon fiber
   20% (Vol.) Teflon TFE fiber
   20% (Vol.) Teflon TFE-6 resin, and
   40% (Vol.) HMWPE
(b) 20% (Vol.) carbon fiber,
   15% (Vol.) Teflon TFE fiber,
   15% (Vol.) Teflon TFE-6 resin, and
   50% (Vol.) HMWPE These formulations are banded at a temperature in the range of 100° F. to 150° F. (preferably 120° F.) are rolled at a temperature in the range of 230° F. to 300° F. (preferably 270° F.) and are sintered at a temperature in the range of 500° F. to 540° F., a pressure in the range of 500 to 2500 psi and for a period from 1 to 4 minutes.

Still another formulation which provides a white, tough material having low friction and low wear is a combination of 50% to 85% (Vol.) HMWPE and equal parts of Teflon TFE fiber and Teflon TFE-6 resin. This composition is rolled at a temperature in the range from 200° F. to 300° F. and is sintered at a temperature in the range from 350° F. to 440° F., at a pressure between 200 and 1,000 psi and for periods up to 2 minutes.

It has been unexpectedly found that with such high percentages of the HMWPE the absence of the Teflon TFE resin appears to prevent adequate cohesion of the structure during rolling. It is postulated that the resin provides internal lubrication which allows the proper cohesion of the composition during the rolling process. The addition of at least 0.5 percent (Vol.) of this resin appears to be adequate for the desired cohesion.

As used herein "high molecular weight polyethylene" shall means polyethylene having a molecular weight greater than about one million such as the Hercules Corporation product sold under the trademark "Hi Fax 1900".

The method of producing these additional compositions of wear material of the present invention are substantially as hereinabove described except that formulation and temperature ranges are modified as previously mentioned with respect to each of said formulations to adjust for the particular properties of each component and to produce the preferred composition of material with each formulation.

The wear material of the present invention has a particular application for in vivo implantation when bio-compatible materials are used but may have other applications not limited to biocompatible materials.

From the foregoing it can be seen that the improved wear material results from a combination of a filler element such as carbon fibers or polytetrafluoroethylene fibers in a matrix of a perfluorinated high polymer resin alone or in combination with a high molecular weight polyethylene resin with the orientation of the fibers being controlled by the method of preparing the material so that they are generally parallel to the material surface which orientation decreases friction and increases wear resistance of the material.

What is claimed is:

1. A composition of matter comprising,
a filler element,
a perfluorinated high polymer resin sintered with said filler element to retain said filler element,
said perfluorinated high polymer resin being selected from the group consisting of polytetrafluoroethylene, polyhexafluropropylene, and a copolymer of hexafluoropropylene and tetrafluroethylene,
said filler element being distributed throughout said material, being selected from the group consisting of, fluorinated carbon particles, fluorinated carbon fibers, surface-fluorinated polyimide fibers, surface-fluorinated polyimide particles surface-fluorinated hydrocarbon particles, surface-fluorinated hydrocarbon fibers, polytetrafluoroethylene fibers, and combinations thereof, the fibers of said filler element being oriented substantially parallel to the surface of the material so that the fibers whose ends lie on or near the surface do not have a tendency to break off,
said filler element being approximately 15 to 65 volume percent of said composition,
the critical surface tension of the filler element closely approximately the critical surface tension of the perfluorinated high polymer resin and
said sintered resin and filler element being suitable for in vivo implantation as a wear material.

2. A composition of matter suitable for in vivo implantation according to claim 1 wherein
the filler element is polytetrafluoroethylene fibers, and
there is sintered with said perfluorinated high polymer resin and polytetrafluoroethylene fibers from 40 to about 85 volume percent of a high molecular weight polyethylene resin.

3. The composition of claim 2, wherein
said high molecular weight polyethylene resin comprises from 40 to 50 percent by volume of said composition and
there is about 20 volume percent carbon fibers with about 30 to 40 volume percent of said polytetrafluoroethylene fiber and resin, each being present in substantially equal proportions.

4. The composition of claim 2, wherein
said high molecular weight polyethylene resin comprises from 50 to 85 percent by volume of said composition,
said perfluorinated high polymer resin is polytetrafluoroethylene and
said resin and fiber present, in substantially equal proportions, combined comprise from 15 to 50 percent by volume of said composition.

5. A composition of matter comprising,
a carbon element, and
a perfluorinated high polymer resin selected from the group consisting of polytetrafluoroethylene, polyhexafluoropropylene, and a copolymer of hexafluoropropylene and tetrafluoroethylene and said perflurinated resin is sintered with said carbon element and said carbon element being selected from the group consisting of fluorinated carbon fibers, fluorinated carbon particles and combinations thereof and wherein said carbon element has been fluorinated to reduce its critical surface tension to approximately 20 dynes per centimeter whereby the critical surface tension of fibers closely approximates the critical surface tension of the perfluorinated high polymer resin, and
said carbon element being approximately 40 percent by volume of said composition.

6. A composition of material suitable for in vivo implantation according to claim 5 wherein said resin is polytetrafluoroethylene.

7. A composition of material suitable for in vivo implantation according to claim 5, including carbon particles.

8. A composition of material suitable for in vivo implantation according to claim 7, wherein
the ratio of fibrous carbon to particulate carbon is in the range from 1 to 1 to 5 to 1.

9. The composition of claim 5 wherein
said material has low friction high wear surfaces resulting from the mixture of the components being rolled into sheet form prior to the sintering of said resin.

10. The composition of claim 9 wherein
said carbon element is in the range of from 15 to 65 percent by volume of said composition.

11. A composition of materials comprising
carbon fibers, and
a perfluorinated high polymer resin sintered with said carbon fibers to retain said fibers,
said perfluorinated high polymer resin being selected from a group consisting of polytetrafluoroethylene, polyhexafluoropropylene, and a copolymer of hexafluoropropylene and tetrafluoroethylene,
said carbon fibers being oriented substantially parallel to the surface of the material so that the fibers whose ends lie on or near the surface of the material do not have a tendency to break off,
said carbon fibers having been fluorinated to reduce their critical surface tension to approximately 20 dynes per centimeter whereby the critical surface tension of said fibers closely approximates the critical surface tension of the perfluorinated high polymer resin.

12. The composition of claim 11 wherein
said carbon fibers are 40 percent by volume of composition.

13. The composition of claim 2, wherein the perfluorinated high polymer resin is polytetrafluoroethylene and is present in an amount of from 0.5 volume percent up to an amount which is equivalent to the amount of polytetrafluoroethylene fibers present in said composition.

* * * * *